(12) United States Patent
Dong et al.

(10) Patent No.: US 9,581,495 B2
(45) Date of Patent: Feb. 28, 2017

(54) SPECTRAL ANALYSIS DEVICE BASED ON BRILLOUIN DYNAMIC GRATING AND ANALYSIS METHOD THEREOF

(71) Applicant: Harbin Institute of Technology, Harbin, Heilongjiang Province (CN)

(72) Inventors: Yongkang Dong, Harbin (CN); Taofei Jiang, Harbin (CN); Dengwang Zhou, Harbin (CN); Zhiwei Lv, Harbin (CN)

(*) Notice: Subject to any disclaimer, the term of this patent is extended or adjusted under 35 U.S.C. 154(b) by 0 days.

(21) Appl. No.: 14/909,948

(22) PCT Filed: Jun. 6, 2014

(86) PCT No.: PCT/CN2014/079418
§ 371 (c)(1),
(2) Date: Feb. 3, 2016

(87) PCT Pub. No.: WO2014/198201
PCT Pub. Date: Dec. 18, 2014

(65) Prior Publication Data
US 2016/0187198 A1    Jun. 30, 2016

(30) Foreign Application Priority Data
Jun. 9, 2013  (CN) .......................... 2013 1 0231671

(51) Int. Cl.
*G01J 3/18*  (2006.01)
*G01J 3/02*  (2006.01)
(Continued)

(52) U.S. Cl.
CPC ............... *G01J 3/18* (2013.01); *G01J 3/0218* (2013.01); *G01J 3/0224* (2013.01);
(Continued)

(58) Field of Classification Search
CPC ..... G01N 2021/4709; G01N 2021/638; G01N 2201/088; G01D 5/35364; G01D 5/268;
(Continued)

(56) References Cited

U.S. PATENT DOCUMENTS

| | | | |
|---|---|---|---|
| 7,679,732 B2 * | 3/2010 | Hotate ................. | G01M 11/088 356/73.1 |
| 2008/0193126 A1 * | 8/2008 | Yamamoto ............. | G01K 11/32 398/34 |

(Continued)

OTHER PUBLICATIONS

Dong, Yongkang et al., "Sub-MHz ultrahigh-resolution optical spectometry based on Brillouin dynamic gratings," May 12, 2014, Optics Letters, vol. 39, No. 10, pp. 2967-2970.*

*Primary Examiner* — Gordon J Stock, Jr.
(74) *Attorney, Agent, or Firm* — Novoclaims Patent Services LLC; Mei Lin Wong

(57) ABSTRACT

A spectroscopic analysis device based on Brillouin dynamic grating and its analysis method, which provides high resolution and large measuring range at the same time. The device includes a laser device (1), a fiber optic coupler device (2), a first fiber amplifier device (3), a first isolator (4), a first polarization controller (5), a second polarization controller (6), a single-sideband modulation modulator (7), a second fiber amplifier device (8), a second isolator (9), a third polarization controller (10), a single-mode fiber (11), a polarization beam splitter (12), a circulator (13), a photodetector (14), a data acquisition card (15), a fourth polarization controller (16) and a microwave source (17). The method utilizes the Brillouin scattering of two beams of pump light in optical fiber forming Brillouin dynamic gratings as the spectral element and achieve a sub-MHz resolution.

5 Claims, 1 Drawing Sheet

(51) Int. Cl.
  *G01J 3/44* (2006.01)
  *G01N 21/63* (2006.01)
  *G01J 3/12* (2006.01)

(52) U.S. Cl.
  CPC ..... *G01J 3/4412* (2013.01); *G01J 2003/1291* (2013.01); *G01N 2021/638* (2013.01)

(58) Field of Classification Search
  CPC ........... G01M 11/319; G01J 2003/1291; G01J 3/0218; G01J 3/0224; G01J 3/18; G01J 3/4412
  See application file for complete search history.

(56) References Cited

U.S. PATENT DOCUMENTS

| | | | |
|---|---|---|---|
| 2010/0225900 A1* | 9/2010 | Hotate | G01M 11/3181 356/73.1 |
| 2013/0025374 A1* | 1/2013 | Voskoboinik | G01D 5/35303 73/655 |
| 2014/0022536 A1* | 1/2014 | Peled | G01M 11/3172 356/73.1 |
| 2014/0083197 A1* | 3/2014 | Zadok | H04B 10/071 73/800 |
| 2014/0098408 A1* | 4/2014 | Williams | G02F 3/026 359/108 |
| 2016/0273999 A1* | 9/2016 | Hotate | G01M 11/3181 |

\* cited by examiner

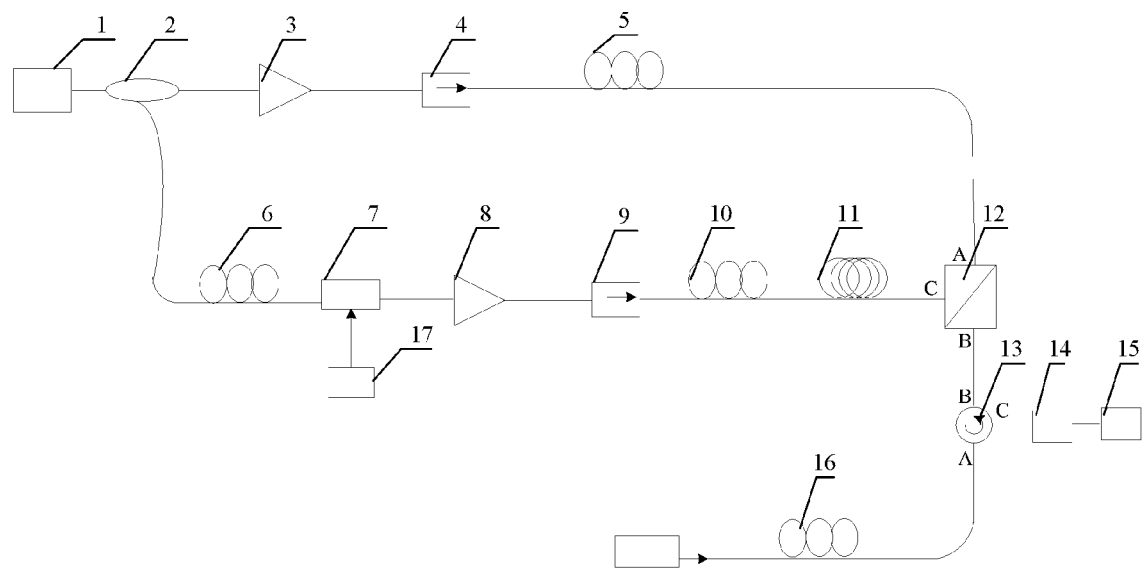

SPECTRAL ANALYSIS DEVICE BASED ON BRILLOUIN DYNAMIC GRATING AND ANALYSIS METHOD THEREOF

CROSS REFERENCE OF RELATED APPLICATION

This is a national phase national application of an international patent application number PCT/CN2014/079418 with a filing date of Jun. 6, 2014, which claimed priority of three foreign applications in China as follow: application number 201310231671.4 and filing date Jun. 9, 2013. The contents of these specifications, including any intervening amendments thereto, are incorporated herein by reference.

BACKGROUND OF THE PRESENT INVENTION

Field of Invention

The present invention relates to a spectroscopic analysis device based on Brillouin dynamic grating and its analysis method, which belongs to the technology of spectroscopic analysis.

Description of Related Arts

The key for spectroscopic analysis devices is how to obtain a high optical wavelength resolution. The method of reducing the Brillouin gain bandwidth can obtain a wavelength resolution of 0.064 pm (8 MHz) (Stefan PreuBler, Andrzej Wiatrek, Kambiz Jamshidi, and Thomas Schneider "Ultrahigh-resolution Spectroscopy Based on the Bandwidth Reduction of Stimulated Brillouin," IEEE Photonics Technology Letters, 23, 1118-1120, 2011). At present, the spectroscopic analysis devices with the highest wavelength resolution for commercial use is the AP204xB series ultrahigh resolution optical spectrum analyzer manufactured by APEX Company, which is based on the interference principle between signal and built-in TLS and has a wavelength resolution of only 0.04 pm (5 MHz).

The major spectral elements in spectroscopic analysis devices includes Volume gratings and Fabry-Perot interferometer. Since volume grating is limited by the technological process, the length of grating is limited and limiting the further increase of resolution of the spectroscopic analysis devices. In addition, during the manufacturing process of volume gratings, defects in manufacturing also impose a limit to resolution and precision of the spectroscopic analysis devices, and the level of precision can only reach 5 pm-10 pm. The spectroscopic analysis devices which employ Fabry-Perot interferometer as the spectral element are also limited by the actual manufacturing process. Since measuring range and resolution are a pair of contradictory parameters, a high resolution cannot be ensured under a large measuring range condition.

SUMMARY OF THE PRESENT INVENTION

An objective of the present invention is to solve the problems of failure to obtain high resolution under the condition of large measuring range with conventional spectral element of spectrometer by providing a spectroscopic analysis device based on Brillouin dynamic grating and its analysis method.

According to a spectroscopic analysis device based on Brillouin dynamic grating of the present invention, the spectroscopic analysis device comprising: a laser device, a fiber optic coupler device, a first fiber amplifier device, a first isolator, a first polarization controller, a second polarization controller, a single-sideband modulation modulator, a second fiber amplifier device, a second isolator, a third polarization controller, a single-mode fiber, a polarization beam splitter, a circulator, a photodetector, a data acquisition card, a fourth polarization controller and a microwave source, the laser device emits a laser beam which is divided into two beams of pump light through the fiber optic coupler device, the first beam of pump light is incident to the first isolator after magnifying processing through the first fiber amplifier device, then the emission light from the first isolator is incident to the polarization controller, after processing an adjustment of a polarization state through the first polarization controller, the first beam of pump light is incident to an A-port of the polarization beam splitter;

the second beam of pump light is incident to the single-sideband modulation modulator after processing an adjustment of a polarization state through the second polarization controller, the frequency provided by the microwave source to the single-sideband modulation modulator is the modulation frequency of Brillouin frequency shift, an optical shifted lower frequency from the single-sideband modulation modulator is incident to the second fiber amplifier device, the second beam of pump light is incident to the second isolator after magnifying processing through the second fiber amplifier device, then the emission light from the second isolator is incident to the third polarization controller, after processing an adjustment of a polarization state through the third polarization controller, the second beam of pump light is incident to the single-mode fiber, the single-mode fiber has an output terminal connecting to a C-port of the polarization beam splitter;

the light for testing is incident to an A-port of the circulator after processing an adjustment of a polarization state through the fourth polarization controller and then incident to a B-port of the polarization beam splitter through a B-port of the circulator, then incident to the single-mode fiber through a C-port of the polarization beam splitter, the light for testing is incident to the c-port of the polarization beam splitter again after reflecting through the single-mode fiber and is emitted from the B-port of the polarization beam splitter, the light for testing emitted from the B-port of the polarization beam splitter is incident to the B-port of the circulator, then is incident to an optical signal receiving terminal of the photodetector after passing through the C-port of the circulator, the photodetector comprises a signal output terminal connecting to a signal acquisition input terminal of the data acquisition card.

The first fiber amplifier and the second fiber amplifier are both erbium-doped fiber amplifier.

The laser device is a tunable laser device.

A spectroscopic analysis method based on Brillouin dynamic grating according to the above spectroscopic analysis device based on Brillouin dynamic grating comprises the steps of:

adjusting the first polarization controller such that the first beam of pump light is passing completely through the A-port of the polarization beam splitter and is output from the C-port of the polarization beam splitter; adjusting the second polarization controller and the third polarization controller such that the second beam of pump light is under the same polarization state as the first beam of pump light, thereby the first beam of pump light and the second beam of pump light has the maximum stimulated Brillouin scattering in the single-mode fiber so as to form the strongest Brillouin dynamic grating;

adjusting the fourth polarization controller such that the light for testing is passing completely through the B-port of the polarization beam splitter and is output from the C-port of the polarization beam splitter, at this point, the light for testing is under a polarization state perpendicular to the polarization state of the first beam of pump light and the second bean of pump light, then adjusting a frequency of the first beam of pump light so that the frequency of the first beam of pump light is the same as the frequency of the light for testing, therefore the light for testing in the Brillouin dynamic grating which is incident to the single-mode fiber is reflected and sequentially passing through the C-port of the polarization beam splitter, the B-port of the polarization beam splitter, the B-port of the circulator and the C-port of the circulator to the photodetector, and then collected by the data acquisition card;

scanning the laser device such that a frequency variation range of the first beam of pump light covers a spectrum of the light for testing and obtaining a complete spectrum of the light for testing so as to realize a spectrum analysis for the light for testing.

The advantageous effect of the present invention:

The present invention utilizes Brillouin dynamic grating in single-mode fiber as the spectral element, the Brillouin dynamic grating in single-mode fiber is formed from the stimulated Brillouin scattering during light transmission in the single-mode fiber. The Brillouin dynamic grating is distributed along the entire optical fiber and is capable of achieving a few hundred meters to several kilometers, which is far greater than the length in volume holographic grating while the Brillouin dynamic grating being formed is more uniformly distributed. Since the length of the Brillouin dynamic grating formed can be very long, it is possible to provide a very narrow reflection band for the grating, and hence to achieve a Brillouin dynamic grating spectrometer with resolution of sub-MHz magnitude. The use of broad bandwidth tunable laser as the pump light can realize the broad measurement range at C+L bandwidth. Accordingly, the characteristics of high resolution, broad range of measurement, high precision and good reliability can be achieved. The spectroscopic analysis device utilizes the standard single-mode optical fiber transmission as the light transmission medium, which has good compatibility and low insertion loss with the existing optical fiber communication systems. The present invention can be widely used in optical fiber communication systems for detection and diagnosis of optical signal transmission and is capable of achieving high spectral resolution in DWDM system, wide measuring range and precision measurement in reflection and absorption spectra of a medium.

The device and method of the present invention can provide extremely high resolution, good signal to noise ratio and good reliability to the spectrum of the light for testing, while its follow-up processing for the spectrum is simple.

BRIEF DESCRIPTION OF THE DRAWINGS

FIG. 1 is a schematic diagram of the optical path of the spectroscopic analysis device based on Brillouin dynamic grating according to the preferred embodiment of the present invention.

DETAILED DESCRIPTION OF THE PREFERRED EMBODIMENT

Embodiment 1: This embodiment is further described in connection with FIG. 1 as follows. According to this embodiment, a spectroscopic analysis device based on Brillouin dynamic grating comprises a laser device 1, a fiber optic coupler device 2, a first fiber amplifier device 3, a first isolator 4, a first polarization controller 5, a second polarization controller 6, a single-sideband modulation modulator 7, a second fiber amplifier device 8, a second isolator 9, a third polarization controller 10, a single-mode fiber 11, a polarization beam splitter 12, a circulator 13, a photodetector 14, a data acquisition card 15, a fourth polarization controller 16 and a microwave source 17, the laser device 1 emits a laser beam which is divided into two beams of pump light through the fiber optic coupler device 2, the first beam of pump light is incident to the first isolator 4 after magnifying processing through the first fiber amplifier device 3, then the emission light from the first isolator 4 is incident to the polarization controller 5, after processing an adjustment of a polarization state through the first polarization controller 5, the first beam of pump light is incident to an A-port of the polarization beam splitter 12;

the second beam of pump light is incident to the single-sideband modulation modulator 7 after processing an adjustment of a polarization state through the second polarization controller 6, the frequency provided by the microwave source 17 to the single-sideband modulation modulator 7 is the modulation frequency of Brillouin frequency shift, an optical shifted lower frequency from the single-sideband modulation modulator 7 is incident to the second fiber amplifier device 8, the second beam of pump light is incident to the second isolator 9 after magnifying processing through the second fiber amplifier device 8, then the emission light from the second isolator 9 is incident to the third polarization controller 10, after processing an adjustment of a polarization state through the third polarization controller 8, the second beam of pump light is incident to the single-mode fiber 11, the single-mode fiber 11 has an output terminal connecting to a C-port of the polarization beam splitter 12;

the light for testing is incident to an A-port of the circulator 13 after processing an adjustment of a polarization state through the fourth polarization controller 16 and then incident to a B-port of the polarization beam splitter 12 through a B-port of the circulator 13, then incident to the single-mode fiber 11 through a C-port of the polarization beam splitter 12, the light for testing is incident to the c-port of the polarization beam splitter 12 again after reflecting through the single-mode fiber 11 and is emitted from the B-port of the polarization beam splitter 12, the light for testing emitted from the B-port of the polarization beam splitter 12 is incident to the B-port of the circulator 13, then is incident to an optical signal receiving terminal of the photodetector 14 after passing through the C-port of the circulator 13, the photodetector 14 comprises a signal output terminal connecting to a signal acquisition input terminal of the data acquisition card 15.

According to this embodiment, a laser device 1 is employed for laser beam emission. The laser beam is split into two pump light through the fiber optic coupler device 2. The first fiber amplifier device 3 magnifies the first beam of pump light to the required power. The first isolator 4 is used to prevent the light transmission from reverse direction to enter the first fiber amplifier device 3 and cause damage the first fiber amplifier device 3. The single-sideband modulation modulator 7 is powered by a DC power supply to provide operating voltage. The second isolator 9 is used to prevent the light transmission from reverse direction to enter the second fiber amplifier device 8 and cause damage to the second fiber amplifier device 8. The selection of laser device 1 can be external cavity lasers (ECL).

According to the requirements, the present invention can include an Erbium-doped fiber magnifier positioned between the light for testing and the fourth polarization controller 16 for amplifying the light for testing to the required power.

According to this embodiment, the splitting ratio of the fiber optic coupler device 2 can be 50:50, or can be selected according to actual need to 90:10, 73:30 or 95:5.

Embodiment 2: This embodiment provides further description for embodiment 1. According to this embodiment, both the first fiber amplifier 3 and the second fiber amplifier 8 are erbium-doped fiber amplifier.

Embodiment 3: This embodiment provides further description for embodiment 1 or 2. According to this embodiment, the laser device 1 is a tunable laser device.

Embodiment 4: This embodiment is described in connection with FIG. 1 as follows. According to this embodiment, the spectroscopic analysis device based on Brillouin dynamic grating according to embodiment 1, 2 or 3 comprises a spectroscopic analysis method based on Brillouin dynamic grating, which comprises the steps of:

adjusting the first polarization controller 5 such that the first beam of pump light is passing completely through the A-port of the polarization beam splitter 12 and is output from the C-port of the polarization beam splitter 12; adjusting the second polarization controller 6 and the third polarization controller 10 such that the second beam of pump light is under the same polarization state as the first beam of pump light, thereby the first beam of pump light and the second beam of pump light has the maximum stimulated Brillouin scattering in the single-mode fiber 11 so as to form the strongest Brillouin dynamic grating;

adjusting the fourth polarization controller 16 such that the light for testing is passing completely through the B-port of the polarization beam splitter 12 and is output from the C-port of the polarization beam splitter 12, at this point, the light for testing is under a polarization state perpendicular to the polarization state of the first beam of pump light and the second bean of pump light, then adjusting a frequency of the first beam of pump light so that the frequency of the first beam of pump light is the same as the frequency of the light for testing, therefore the light for testing in the Brillouin dynamic grating which is incident to the single-mode fiber 11 is reflected and sequentially passing through the C-port of the polarization beam splitter 12, the B-port of the polarization beam splitter 12, the B-port of the circulator 13 and the C-port of the circulator 13 to the photodetector 14, and then collected by the data acquisition card 15;

scanning the laser device 1 such that a frequency variation range of the first beam of pump light covers a spectrum of the light for testing and obtaining a complete spectrum of the light for testing so as to realize a spectrum analysis for the light for testing.

According to this embodiment, the light for testing is emitted from the C-port of the polarization beam splitter 12. When its frequency is the same as the first beam of pump light, the light for testing which is incident to the Brillouin dynamic gratings in the single-mode fiber 11 is reflected.

The process of scanning is carried out to the frequency of the light output from the laser device 1. The light for testing is only reflected only when the frequency of the light output from the laser device is the same as the light for testing. Therefore, based on the frequency of the light output from the laser device, the frequency of the light for testing is determined, hence spectral analysis is realized.

According to this embodiment, the Brillouin scattering of two beams of pump light in the optical fiber is used to form the Brillouin dynamic gratings, which is used as the spectral element, thus spectral analysis by Brillouin dynamic gratings at a sub-MHz resolution is achieved.

What is claimed is:

1. A spectroscopic analysis device based on Brillouin dynamic grating, characterized in that, said spectroscopic analysis device comprising: a laser device (1), a fiber optic coupler device (2), a first fiber amplifier device (3), a first isolator (4), a first polarization controller (5), a second polarization controller (6), a single-sideband modulation modulator (7), a second fiber amplifier device (8), a second isolator (9), a third polarization controller (10), a single-mode fiber (11), a polarization beam splitter (12), a circulator (13), a photodetector (14), a data acquisition card (15), a fourth polarization controller (16) and a microwave source (17), said laser device (1) emits a laser beam which is divided into two beams of pump light through said fiber optic coupler device (2), said first beam of pump light is incident to said first isolator (4) after magnifying processing through said first fiber amplifier device (3), then the emission light from said first isolator (4) is incident to said first polarization controller (5), after processing an adjustment of a polarization state through said first polarization controller (5), said first beam of pump light is incident to an A-port of said polarization beam splitter (12);

said second beam of pump light is incident to said single-sideband modulation modulator (7) after processing an adjustment of a polarization state through said second polarization controller (6), a frequency provided by said microwave source (17) to said single-sideband modulation modulator (7) is a modulation frequency of Brillouin frequency shift, an optical shifted lower frequency from said single-sideband modulation modulator (7) is incident to said second fiber amplifier device (8), said second beam of pump light is incident to said second isolator (9) after magnifying processing through said second fiber amplifier device (8), then the emission light from said second isolator (9) is incident to said third polarization controller (10), after processing an adjustment of a polarization state through said third polarization controller (8), said second beam of pump light is incident to said single-mode fiber (11), said single-mode fiber (11) has an output terminal connecting to a C-port of said polarization beam splitter (12);

a light for testing is incident to an A-port of said circulator (13) after processing an adjustment of a polarization state through said fourth polarization controller (16) and then incident to a B-port of said polarization beam splitter (12) through a B-port of said circulator (13), then incident to said single-mode fiber (11) through a C-port of said polarization beam splitter (12), the light for testing is incident to said c-port of said polarization beam splitter (12) again after reflecting through said single-mode fiber (11) and is emitted from said B-port of said polarization beam splitter (12), the light for testing emitted from said B-port of said polarization beam splitter (12) is incident to said B-port of said circulator (13), then is incident to an optical signal receiving terminal of said photodetector (14) after passing through said C-port of said circulator (13), said photodetector (14) comprises a signal output terminal connecting to a signal acquisition input terminal of said data acquisition card (15).

2. The spectroscopic analysis device based on Brillouin dynamic grating according to claim 1, characterized in that, said laser device (1) is a tunable laser device.

3. A spectroscopic analysis method for the spectroscopic analysis device based on Brillouin dynamic grating according to claim 1, characterized in that, said method comprises the steps of:
- adjusting said first polarization controller (5) such that said first beam of pump light is passing completely through said A-port of said polarization beam splitter (12) and is output from said C-port of said polarization beam splitter (12);
- adjusting said second polarization controller (6) and said third polarization controller (10) such that said second beam of pump light is under the same polarization state as said first beam of pump light, thereby said first beam of pump light and said second beam of pump light has a maximum stimulated Brillouin scattering in said single-mode fiber (11) so as to form a strongest Brillouin dynamic grating;
- adjusting said fourth polarization controller (16) such that the light for testing is passing completely through said B-port of said polarization beam splitter (12) and is output from said C-port of said polarization beam splitter (12), at this point, the light for testing is under a polarization state perpendicular to the polarization state of said first beam of pump light and said second bean of pump light, then adjusting a frequency of said first beam of pump light so that the frequency of said first beam of pump light is the same as the frequency of the light for testing, therefore the light for testing in the Brillouin dynamic grating which is incident to said single-mode fiber (11) is reflected and sequentially passing through said C-port of said polarization beam splitter (12), said B-port of said polarization beam splitter (12), said B-port of said circulator (13) and said C-port of said circulator (13) to said photodetector (14), and then collected by said data acquisition card (15);
- scanning said laser device (1) such that a frequency variation range of said first beam of pump light covers a spectrum of the light for testing and obtaining a complete spectrum of the light for testing so as to realize a spectrum analysis for the light for testing.

4. The spectroscopic analysis device based on Brillouin dynamic grating according to claim 1, characterized in that, said first fiber amplifier (3) and said second fiber amplifier (8) are both erbium-doped fiber amplifier.

5. The spectroscopic analysis device based on Brillouin dynamic grating according to claim 4, characterized in that, said laser device (1) is a tunable laser device.

* * * * *